United States Patent [19]

Freeland

[11] 4,332,038
[45] Jun. 1, 1982

[54] ARTIFICIAL HAND

[76] Inventor: John L. Freeland, 280 Pennsylvania, Apt. 1, San Francisco, Calif. 94107

[21] Appl. No.: 218,186

[22] Filed: Dec. 19, 1980

[51] Int. Cl.³ .............................................. A61F 1/06
[52] U.S. Cl. ....................................................... 3/12.6
[58] Field of Search ..................... 3/12, 12.1, 12.4–12.8

[56] References Cited

U.S. PATENT DOCUMENTS

| | | | |
|---|---|---|---|
| 493,440 | 3/1893 | Minzey | 3/12.6 |
| 1,390,802 | 9/1921 | McKay | 3/12.8 |
| 2,568,299 | 9/1951 | Philpott | 3/12.7 |
| 2,669,727 | 2/1954 | Opuszenski | 3/12.7 |
| 4,225,983 | 10/1980 | Radocy et al. | 3/12.7 X |

FOREIGN PATENT DOCUMENTS

| | | | |
|---|---|---|---|
| 733179 | 3/1943 | Fed. Rep. of Germany | 3/12 |
| 901583 | 1/1954 | Fed. Rep. of Germany | 3/12 |
| 1108875 | 9/1955 | France | 3/12 |

*Primary Examiner*—Ronald L. Frinks
*Attorney, Agent, or Firm*—Owen, Wickersham & Erickson

[57] ABSTRACT

An artificial hand has a stationary wrist and two fingers and a thumb pivotal from a horizontal axis in the wrist. The thumb may have two separable portions, one of which is pivotal away from the other along a generally vertical axis by manual prepositioning. This enables rounded objects such as doorknobs to be grasped by the curved main finger and the two thumb portions, making stable three-point contact. The two fingers are pivotal along the wrist axis in a fixed range of motion with respect to the thumb, and a spring urges the fingers toward a normal open position. Tension of a sheathed cable fitted to a standard body harness closes the fingers to the thumb, enabling a powerful grip. The second finger is straight and normally remains alongside the curved finger until, upon closure of the curved finger and contact to its tip with the thumb, further cable tension closes the straight finger against the thumb to grip small or flat, thin objects. A special link between the cable and the fingers is provided for this purpose.

28 Claims, 6 Drawing Figures

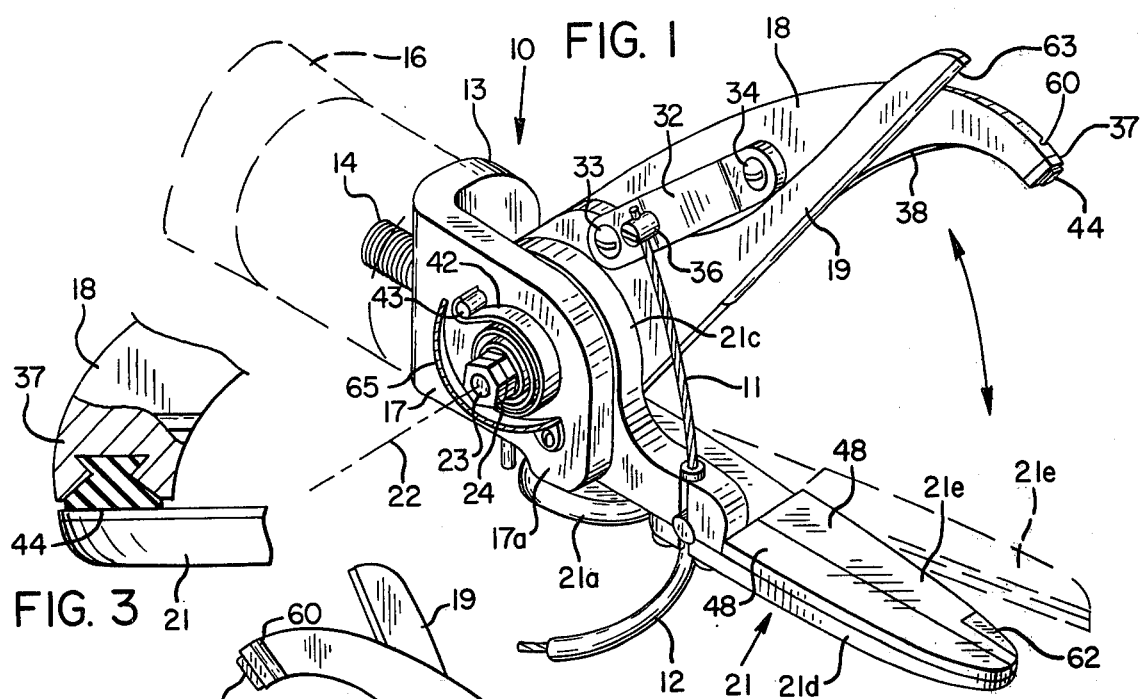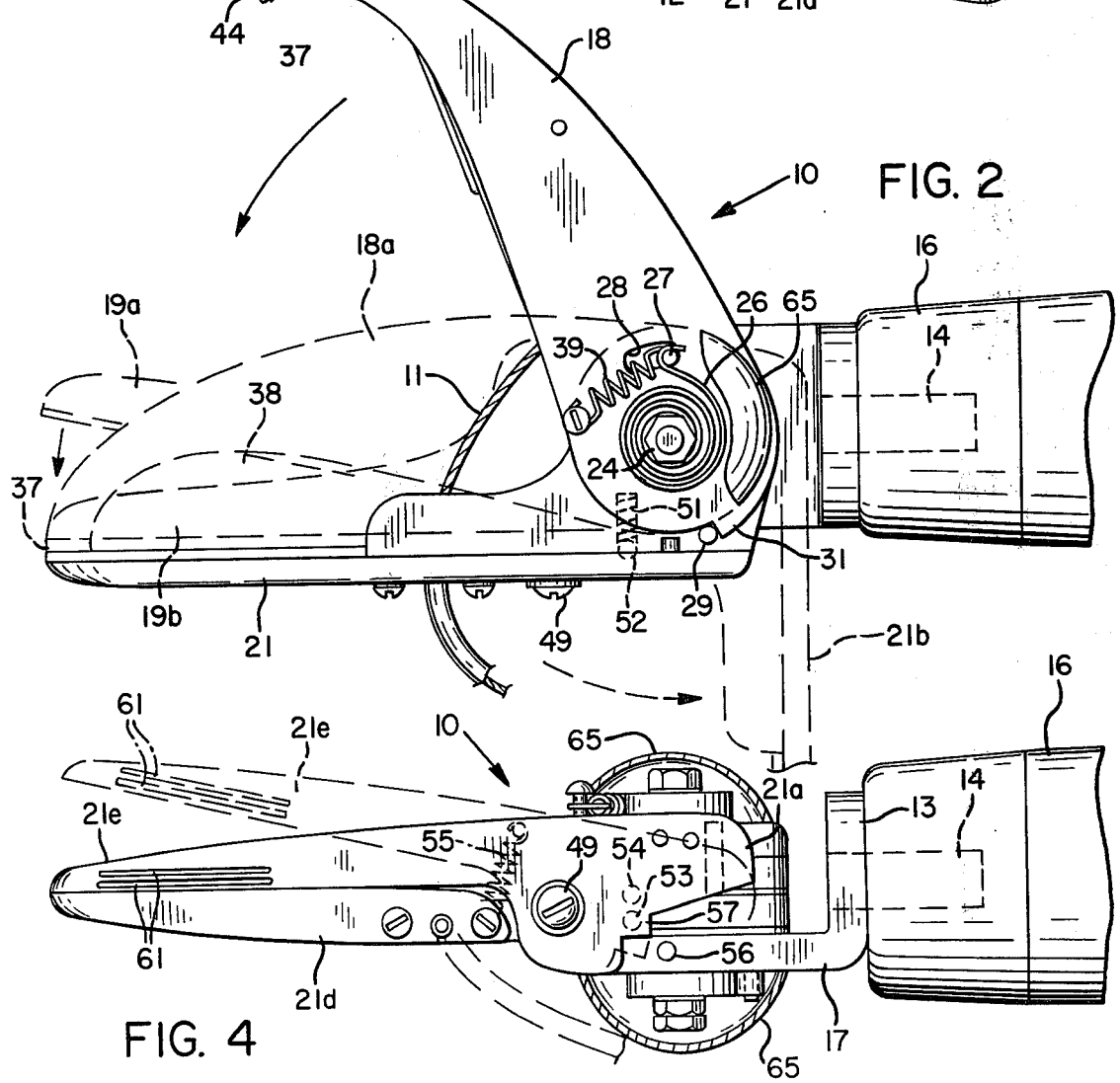

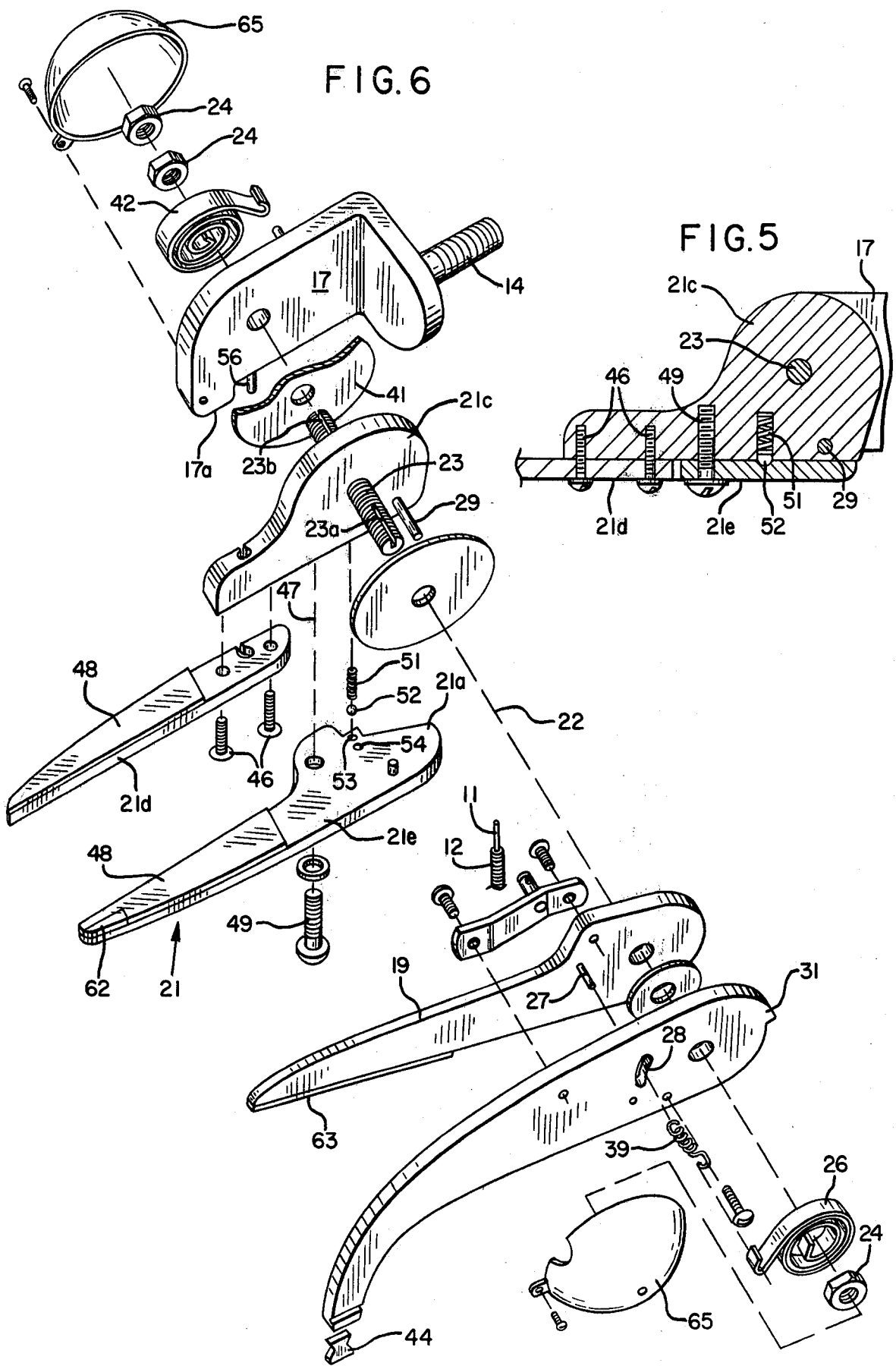

ARTIFICIAL HAND

BACKGROUND OF THE INVENTION

The invention relates to artificial mechanical hands, and more particularly to an improved mechanical hand with multiple prehension capability, especially suitable for bilaterals, or double amputees.

For unilaterals, or single amputees, a mechanical hand often takes the form of a simple split hook of the type shown, for example, in U.S. Pat. No. 1,042,413. This type of artificial hand unusually has a spring or elastic band urging the two hook sections together to grasp objects between them, with the sections openable by the action of a cable attached to a body harness. Another example of this type of artificial hand is shown in U.S. Pat. No. 1,206,753.

Bilaterals, with no natural hand for the more difficult grasping functions, need artificial hands with more complete prehension capability than is afforded by the hook described above. A number of more complex artificial hand mechanisms have been suggested, as shown for example in U.S. Pat. Nos. 2,422,530, 2,487,724, 2,409,884, 2,853,711, 3,413,658, and 4,016,607.

The disadvantages of these prior art devices have been that they are either too complicated to be economically feasible, they have been difficult to learn to operate, they have failed to provide important types of prehension capability, or they have been oriented so much toward cosmetic appeal that they necessarily have been very limited in functional advantages.

None of the devices shown in the prior patents provides the degree of prehensile versatility, with the simplicity of construction and operation, as does the present invention described below.

SUMMARY OF THE INVENTION

The artificial hand of the present invention facilitates a combination of important prehension functions in one relatively simple apparatus, operable by a standard sheathed cable connected to a body harness known in the prior art. The hand enables the user to grasp rounded objects such as doorknobs and to easily turn a doorknob, to grasp objects between a finger tip and a thumb, and to grip small or thin objects with an auxiliary finger which forms a line of contact with the flat surface of the thumb. The fingers are urged by a spring toward their open position away from the thumb, and cable tension is effective to close the fingers towards the thumb in a powerful grip. Many prior art mechanical hands worked oppositely, with a spring providing the pressure to close the gripping mechanism and the cable merely opening it.

When cable tension is put to the hand of the invention, the finger tip of a main finger first comes into contact with the relatively stationary thumb. Continued additional tension brings the auxiliary, straight finger into a line of contact with the thumb; and still further cable retraction pivots the entire closed hand, fingers and thumb, downward along a wrist pivot axis, to a position where the hand would be usable for reaching into a breast pocket, for example.

The thumb of the artificial hand preferably is split into two components, one of which is pivotable toward and away from the other. This is for prepositioning the openable thumb portion for functions such as gripping doorknobs, where three points of contact are desirable for a stable grip.

In a preferred embodiment, an artificial hand according to the present invention comprises a support base for connecting to the arm of the user, with a wrist connected to the base and a pivot axis in the wrist. A pivotal main finger is connected along the pivot axis to the wrist, with a downwardly angled finger tip at its ends. Alongside the main finger is a generally straight pivotal finger, also connected along the pivot axis to the wrist and normally in a position spaced angularly back of the finger tip of the main finger, so that the finger tip leads the straight finger as the two fingers are moved downwardly. A thumb extends from the wrist, positioned to be contacted by the fingers in their downward, closed position. Means are provided in association with the main finger and the thumb for enabling grasping of rounded objects between them. There are provided a control cable and cable housing adapted for connection to typical harness apparatus worn on the body of the user, with means connecting the forward end of the cable housing to the thumb and means connecting the forward end of the cable, extending from the housing, to the fingers in such a way that retraction of the cable in the housing pulls the fingers toward the thumb, first contacting the main finger tip with the thumb and then bringing the straight finger toward contact with the thumb on further retraction of the cable. A means is provided for biasing the main finger and the straight finger away from the thumb to their normal open position.

Accordingly, it is among the objects of the invention to provide an improved artificial, mechanical hand capable of fulfilling the needs of bilaterals and providing for multiple forms of prehension from a simple, single-cable actuation system. Other objects, advantages and features of the invention will be apparent from the following description of some preferred embodiments, considered in connection with the accompanying drawings.

DESCRIPTION OF THE DRAWINGS

FIG. 1 is a perspective view showing an artificial hand according to the invention, connected to a prosthetic device at the end of the arm of a user. The hand illustrated is a right hand.

FIG. 2 is a left side elevational view of the hand of FIG. 1.

FIG. 3 is a detailed, partially sectioned view showing a resilient insert in the tip of a finger of the artificial hand.

FIG. 4 is a bottom view of the artificial hand.

FIG. 5 is a sectional view showing the connection of several relatively movable components of the artificial hand of the invention.

FIG. 6 is an exploded view in perspective of the artificial hand.

DESCRIPTION OF THE PREFERRED EMBODIMENTS

In the drawings, FIG. 1 shows an artificial hand 10 according to the invention, preferably employed as a right hand because of the location of a cable and sheath 11 and 12 and the orientation of certain other components.

The hand 10 includes a support base 13 with some form of connection such as a threaded stud 14 for securing to a prosthetic device 16 attached to the arm of the user. Preferably, the support base 13 has a forward extending flange or wrist 17 as shown, from which a main finger 18, a straight finger 19 and a thumb 21 are pivotally supported along a wrist pivot axis 22. A threaded shaft 23 (see also FIG. 6) is advantageously used for supporting the fingers 18 and 19 and the thumb 21 along the axis 22, and nuts 24 at either end and may be employed to retain the assembly together.

The position of the aritifical hand shown in FIGS. 1 and 2 is the normal position. The main finger 18 and the straight finger 19 are biased toward the open position by a spiral spring 26 on the left side of the hand (see FIGS. 2 and 6), secured to the threaded shaft 23 by a slot 23a shown in FIG. 6 and in engagement with a stud pin 27 which extends from the straight finger 19 through an elongated, slot-shaped opening or window 28 of the main finger to its connection with the spring 26 as shown in FIG. 2. The stud 27 and the window 28 are so positioned that both the fingers 18 and 19 receive the force of the spring 26 when the fingers are both in the normal open position shown in FIGS. 1 and 2. However, the straight finger 19 is permitted a small degree of movement downward relative to the main finger 18, while still being under the influence of the spring 26, tending to urge it toward the full open position. The purpose and function of the arrangement will be explained below.

Limitation of upward, opening movement of the fingers 18 and 19 is provided by a stud 29 forming a stop against which an abutment 31 engages (see FIGS. 2 and 6). This limits upward pivotal movement of the main finger 18, since the abutment 31 is on this finger, and also limits movement of the straight finger 19 in the same direction, since the stud 27 extends from the finger and is stopped by the boundary of the window 28 in the main finger.

The cable 11 and sheath 12 are adapted for connection to a standard body harness (not shown) for operation of mechanical hands, with appropriate means connected to the shoulder for pulling the cable 11, retracting it within its sheath 12, which is braced at another point, such as the upper arm. Retraction of the cable moves the two fingers downwardly with respect to the thumb 21, to which the end of the sheath 12 is anchored as shown. The end of the cable 11 is attached to a link 32, which is pivotally connected at spaced locations 33 and 34 to each of the straight finger 19 and the main finger 18, respectively. The link 32, and its connection 36 with the end of the cable 11, are so positioned that retraction of the cable 11 first pulls the main finger 18 downwardly toward the thumb, until it reaches contact with the thumb as illustrated in dashed lines in FIG. 2 with the main finger 18a and the straight finger 19a. The straight finger remains in its normal position with respect to the main finger during this retraction, and objects can be grasped between a tip 37 of the main finger and the thumb, or between a concavely curved portion 38 of the main finger and the thumb.

However, if the cable 11 is retracted further when the fingers are in the positions 18a and 19a shown in FIG. 2, the straight finger 19a will be urged by the pivotal cable link 32 further downwardly, independent of the main finger, until it meets the thumb at a position 19b shown in dashed lines in FIG. 2. This enables the grasping of small, long objects, such as a pencil. In this position both the fingers are urged against the surface of the thumb 21 by the force applied by the cable 11 through the link 32. Only the straight finger 19 is acted upon by the spring 26 in this position, since the stud 27 extending from the straight finger will be at the lower end of the window 28.

When the cable 11 is released, the spiral spring 26 would tend to pull the straight finger back to its position 19a shown in FIG. 2, before the main finger 18 leaves the position 18a shown in FIG. 2. However, in some circumstances it is desirable that the straight finger remain extended, substantially flush with the finger tip 37 of the main finger, during the initial part of the retraction. This is desirable, for example, when the hand is to be inserted in a pocket and the straight finger 19 might snag on the pocket if in its normal position with respect to the main finger 18. Therefore, a tension spring 39 is positioned as shown on the left side of the hand 10, secured to the outside of the main finger 18 and connected to the stud 27 of the straight finger, tending to move the straight finger 19 toward the position 19b shown in FIG. 2 relative to the main finger 18. The force of the spring 39 is considerably lighter than that of the spiral spring 26, but sufficient to partially counterbalance the spring 26 during the initial release of the cable 11, so that the two fingers 18 and 19 do not assume their normal positions relative to one another until they have both moved somewhat away from the thumb 21.

The normal position of the thumb 21 on the wrist or flange 17 is shown in FIGS. 1 and 2 in solid lines. However, the thumb 21, like the fingers 18 and 19, is pivotal along the axis 22. To hold it in the normal, generally straight forward position shown in the figures, a friction washer 41 is positioned between the thumb 21 and the wrist 17, as best seen in the exploded view of FIG. 6. Thus, with a prescribed degree of tightness of the nuts 24 on the threaded shaft 23, the thumb is held in its normal position while the fingers freely rotate along the axis 22.

When desired, the thumb can be moved manually or "prepositioned" to a downwardly pivoted condition, as shown in dashed lines in FIG. 2, with the thumb shown at 21b. The user does this prepositioning by reaching his arm out beyond the point where the fingers contact the thumb, to retract the cable even further. This pulls the thumb to the downwardly pivoted position 21b.

This positioning of the hand is desired, for example, when the user wishes to reach into a breast pocket. Once in this position the fingers and thumb can be used in the normal way, by retraction of the cable 11. When the thumb and fingers are to be returned, the thumb is simply pushed back to its normal position by pushing against a stationary object or against a part of one's body such as a leg, etc. The fingers stay in the same relative position with respect to the thumb (as in FIG. 1), because of the stop and abutment 29 and 31 acting between the thumb 21 and the main finger 18. The normal position is defined as shown in FIG. 1 by a rear portion 21a of the thumb engaging against a forward bottom surface 17a of the wrist 17.

To aid in the manual return of the thumb to the normal position, there may be provided a second spiral spring 42 on the right side of the hand as shown in FIGS. 1 and 6. This spring engages against a stud 43 on the wrist flange 17 and acts on the threaded shaft 23 (via a slot 23b shown in FIG. 6), which preferably is connected to the thumb 21 to urge the shaft 23 and thumb 21 toward the normal position. Friction between the wrist 17 and thumb 21 is preferably sufficient to maintain the thumb in whatever position the user prepositions it, but the spring enables it to be returned with a lighter force.

FIG. 3 shows a resilient tip 44 on the finger tip 37, which may be a replacable element inserted into the finger tip as shown. This enables better grasping of objects between the finger tip and thumb.

As shown in the drawings, particularly FIG. 6, the thumb 21 is made up of several components. A rearward or base portion 21c of the thumb is affixed to the threaded shaft 23, and this may be integral with a stationary portion 21d of the thumb, or it may be affixed thereto by fasteners 46, as shown. The thumb may also include a movable portion 21e, pivotal along a generally vertical axis 47 (FIG. 6) with respect to the remainder of the thumb. This enables the movable portion 21e to swing away from the stationary portion 21d as indicated in dashed lines in FIGS. 1 and 4.

When the thumb portions 21d and 21e are closed, i.e. in their normal position, and the main finger 18 is brought down to the thumb, the finger tip 37 (i.e. the resilient insert 44) engages against the movable portion of the thumb 21e. The straight finger 19 comes down adjacently and engages against the surface of the stationary thumb portion 21d. When the movable thumb portion 21e is opened, by manual prepositioning, the main finger 18 then converges toward the space between the two thumb portions. This provides a three-point set of gripping contacts for engaging thick or rounded objects, particularly those which are to be turned such as doorknobs. A rubber or resilient type surface 48 preferably is included on both thumb portions for better gripping of objects, and this aids considerably in the gripping of rounded objects.

The movable thumb portion 21e may be connected to the thumb base portion 21c by a threaded fastener 49, as best seen in FIGS. 4 and 6. It is maintained in the normal position or the open position by a ball and detent arrangement. As indicated in FIG. 6, this may include a spring 51 urging a ball 52 downwardly from a bore (see FIG. 2) in the portion 21c, for engagement with either of two detents 53 and 54 in the upper surface of the movable thumb portion 21e.

As indicated in broken lines in the bottom view of FIG. 4, a tension spring 55 may be included to urge the movable thumb portion 21e toward the closed position, the spring not being sufficiently strong to overcome the holding action of the ball and detent.

When the thumb portions 21d and 21e are separated, as shown in dashed lines in FIGS. 1 and 4, the hand is sometimes used to pick up heavy objects. For this purpose it is necessary to keep the thumb 21 in the normal position, preventing it from pivoting downwardly (as shown at 21b in FIG. 2). Therefore, a special feature is provided for acting between the movable thumb portion 21e and the wrist 17. As best seen in the bottom view of FIG. 4, this arrangement comprises a stud 56 extending downwardly from the bottom of the wrist 17 and a boss 57 which is clear of the stud 56 in the closed position of the thumb but directly in the path of the stud 56 when the movable thumb portion 21e is pivoted outwardly as shown in dashed lines in FIG. 4. This provides a stop against downward movement of the thumb assembly, even when heavy weights are lifted.

There are several additional features which give the artificial hand of the invention additional versatility, particularly for bilaterals who have no natural hand to supplement the use of the mechanical hand. One such feature is a groove 60 in the side of the finger tip 37 of the curved main finger 18, as shown in FIGS. 2 and 6. The groove 60 can be used to catch an edge of a small object, and the narrow portion of the finger below the groove, between the groove and the tip, enables the user to lift the edge of a small object such as a pop top seal on a can of liquid refreshment, and from there he is able to grasp the object between the pliable finger tip pad 44 and the thumb 21.

As shown in the bottom view of FIG. 4, grooves 61 or other textured surfacing preferably are included in the bottom surface of the movable thumb portion 21e, to aid the user in prepositioning the thumb to the open position.

At the top surface of the movable thumb portion 21e as shown in FIGS. 1 and 6, there may be included a metal corner area 62, in the surface otherwise covered with the resilient high-friction surface material 48. This is helpful in picking up small objects in instances where the resilient material 48 might actually hinder the grasping of the object between the finger tip 37 and the thumb portion 21e.

As indicated in the drawings, the straight finger 19, which converges down onto the non-pivotal thumb portion 21d in a line of contact just adjacent to the separation of the two thumb portions 21d and 21e, may also include a resilient surface strip 63. This further aids in gripping objects or sheet materials such as papers.

An additional feature that preferably is included in the artificial hand 10 of the invention for both aesthetic and functional reasons is a pair of protective cups 65 appropriately secured to the outside of the wrist 17 on the one side and of the main finger 18 on the other side, as shown in FIGS. 1, 2, 4 and 6. These cups 65 improve the appearance of the hand, hiding the springs 42, 26 and 39 and the other hardware associated with them, and also cover these components to prevent their catching or snagging on clothing or other objects.

It should be understood that other features of the artificial hand of the invention may be modified to present a more aesthetic appearance—the fingers may be modified to appear more like human fingers, and the thumb may also be made to appear more like the human. Preferably, these changes are made in such a way as to maintain the functionality of the hand and to avoid excessive cost of manufacture.

It should also be understood that certain modifications can be made to the function of the hand shown in the drawings, without departing from the scope of the invention. For example, the principal purpose of the two-component pivotal thumb is to provide a three-point contact for certain types of gripping, such as doorknobs and other rounded or thick objects. This can be accomplished, for some applications, by simply providing a shaped thumb capable of providing two points of contact without any prior prepositioning movement, the third point of contact being made by the main finger 18. The illustrated split thumb, however, is preferred.

Similarly, for some applications it may be desirable to eliminate the straight finger 19, including the main finger 18 as the only finger converging toward the thumb. For example, if the artificial hand is to be used by a unilateral amputee, rather than a bilateral, or if it is for a bilaterial having a complete artificial hand 10 as illustrated in the drawings as one hand, the other hand may be of a somewhat simplified version, perhaps without the straight finger 19.

It should be further understood that the split thumb, as provided, can take other forms from that shown in the drawing. For example, it may be formed with the portions 21d and 21e both swingable away from one another, rather than the simpler arrangement illustrated wherein only one portion is movable.

Other embodiments and variations to the illustrated preferred embodiment will be apparent to those skilled in the art and may be made without departing from the spirit and scope of the invention as defined in the following claims.

I claim:

1. An artificial hand, comprising:
a support base for connecting to the arm of a user;
a wrist connected to the base, with a pivot axis in the wrist;
a pivotal main finger connected along the pivot axis to the wrist, and having a downwardly angled finger tip at its end;
a generally straight pivotal finger alongside the main finger, also connected along the pivot axis to the wrist, normally in a position spaced angularly back from the finger tip of the main finger;
a thumb extending from the wrist and positioned to be contacted by the fingers in their downward, closed positions;
means associated with the main finger and the thumb for enabling gasping of rounded objects between them;
a control cable and cable housing adapted for connection to harness apparatus worn on the body of the user;
means connecting a forward end of the cable housing to the thumb and means connecting a forward end of the cable, extending from the housing, to the fingers such that retraction of the cable in the housing pulls the fingers toward the thumb, first contacting the main finger tip with the thumb, with further cable retraction moving the straight finger toward contact with the thumb; and
means biasing the main finger and the straight finger away from the thumb toward their normal open position.

2. The artificial hand of claim 1, wherein the thumb is pivotally connected along the pivot axis to the wrist, and including means for retaining the thumb in preselected positions.

3. The artificial hand of claim 2, said means for retaining the thumb in preselected positions comprising a fastener along the pivot axis of the wrist, tightened to urge the thumb toward a stationary portion of the wrist along the pivot axis so that the thumb tends to remain in a preselected position due to friction.

4. The artifical hand of claim 2, further including stop means associated with the thumb and the main finger for limiting the degree of opening movement of the main finger with respect to the thumb.

5. The artificial hand of claim 1, wherein the pivotal main finger is downwardly curved to the finger tip.

6. The artificial hand of claim 1, wherein the finger tip includes a resilient end for helping engage objects between the finger tip and the thumb.

7. The artificial hand of claim 6, wherein the resilient end is a replaceable rubber-like element.

8. The artificial hand of claim 1, wherein the straight pivotal finger includes a strip of resilient, high-friction material positioned to engage the thumb when the straight finger is pivoted toward the thumb.

9. The artificial hand of claim 1, wherein the thumb is generally planar and parallel to the axis of the wrist, and wherein said means for enabling grasping of rounded objects comprises the thumb including two portions, at least one of which is movable relative to the other in a generally horizontal plane between a normal closed position and an open position, with the main finger positioned to converge between the two thumb portions when the thumb portions are in the open position, whereby generally rounded objects such as doorknobs may be gripped at three points.

10. The artificial hand of claim 9, wherein the main finger is downwardly curved and hook-like toward the fingertip, further aiding in the grasping of rounded objects.

11. The artificial hand of claim 9, including releasable means for holding the movable thumb portion in the closed position or in the open position.

12. The artificial hand of claim 11, wherein the releasable holding means comprises a spring-urged ball and two alternative-position detents associated with the thumb portions for holding the movable thumb portion in the open or closed position, allowing prepositioning of the thumb when needed.

13. The artificial hand of claim 11, including spring means urging the thumb portions together.

14. The artificial hand of claim 9, wherein the thumb is also pivotally connected along the pivot axis of the wrist, both thumb portions being pivotal together along the wrist axis, with stop means for limiting opening movement of the main finger away from the thumb and defining the normal open position, and including means associated with the wrist and the movable thumb portion for preventing downward pivotal movement of the thumb on the wrist when the movable thumb portion is in the open position.

15. The artificial hand of claim 14, wherein the means for preventing downward pivotal movement comprises a stud extending from the wrist and an extension on the movable thumb portion, adjacent to the stud, positioned to pass by the stud when the two thumb portions are together and the thumb is pivoted downwardly on the wrist axis, but to abut the stud, preventing downward pivoting of the thumb, when the thumb is in the open position.

16. The artificial hand of claim 1, wherein the means connecting the forward end of the cable to the fingers comprises a link pivotally attached at spaced positions to each finger, outboard of the wrist axis, with the forward end of the cable attached to the link between the two spaced positions.

17. The artificial hand of claim 16, further including a compensator spring connected to the two fingers and urging the straight finger away from its normal position with respect to the main finger, the positions of attachment of the link to the two fingers and of the cable to the link, and the urging force of the compensator spring, being such that retraction of the cable in the housing moves the straight finger toward the thumb only after the finger tip of the main spring has contacted the thumb and such that once the straight finger has been closed on the thumb, and the fingers are reopened by relaxing tension on the cable, the straight finger remains lowered with respect to the main finger during the initial portion of opening of the main finger.

18. The artificial hand of claim 1, wherein the straight finger upon closure is parallel with the thumb, meeting it substantially along a line of contact.

19. The artificial hand of claim 1, wherein the biasing means comprises a spiral spring attached to the wrist and engaging the fingers.

20. The artificial hand of claim 19, wherein the spiral spring is secured to the straight finger, with a stop on the straight finger positioned to engage the main finger only when the straight finger is in its normal position, to urge the main finger toward the open position along with the straight finger.

21. An artificial hand, comprising:
a support base for connecting to the arm of a user;
a wrist connected to the base, with a pivot axis in the wrist;
a pivotal main finger connected along the pivot axis to the wrist, and having a downwardly angled finger tip at its end;
a thumb extending from the wrist and positioned to be contacted by the fingers in its downward, closed position;
means associated with the main finger and the thumb for enabling grasping of rounded objects between them;
a control cable and cable housing adapted for connection to harness apparatus worn on the body of the user;
means connecting a forward end of the cable housing to the thumb and means connecting a forward end of the cable, extending from the housing, to the main finger such that retraction of the cable in the housing pulls the finger toward the thumb to contact the finger tip with the thumb;
means biasing the main finger away from the thumb toward its normal open position.

22. The artificial hand of claim 21, wherein the thumb is pivotally connected along the pivot axis to the wrist, and including means for retaining the thumb in preselected positions.

23. The artificial hand of claim 22, said means for retaining the thumb in preselected position comprising a fastener along the pivot axis of the wrist, tightened to urge the thumb against a stationary portion of the wrist along the pivot axis so that the thumb tends to remain in a preselected position due to friction.

24. The artificial hand of claim 21, wherein the pivotal main finger is downwardly curved to the fingertip.

25. The artificial hand of claim 21, wherein the finger tip includes a resilient end for helping engage objects between the finger tip and the thumb.

26. The artificial hand of claim 21, wherein the thumb is generally planar and parallel to the axis of the wrist, and wherein said means for enabling grasping of rounded objects comprises the thumb including two portions, at least one of which is movable relative to the other about a thumb pivot axis generally perpendicular to the plane of the thumb, between a normal closed position and an open position, with the main finger positioned to converge between the two thumb portions when they are in the open position, whereby generally rounded objects such as doorknobs may be gripped at three points.

27. The artificial hand of claim 26, wherein the main finger is downwardly curved and hook-like toward the finger tip, further aiding in the grasping of rounded objects.

28. The artificial hand of claim 26, wherein only one of the thumb portions is movable, swingable about the thumb pivot axis, with the movable portion positioned to be engaged by the main finger when in the closed position so that the main finger converges between the two thumb portions when the movable portion is in the open position.

* * * * *